United States Patent
Nathan et al.

(10) Patent No.: US 7,030,127 B2
(45) Date of Patent: *Apr. 18, 2006

(54) COMPOSITION AND MEDICAL DEVICES UTILIZING BIOABSORBABLE POLYMERIC WAXES

(75) Inventors: Aruna Nathan, Bridgewater, NJ (US); Joel Rosenblatt, Watchung, NJ (US); Steven C. Arnold, Sparta, NJ (US)

(73) Assignee: Ethicon, Inc., Somerville, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/896,004

(22) Filed: Jun. 29, 2001

(65) Prior Publication Data

US 2003/0003125 A1 Jan. 2, 2003

(51) Int. Cl.
*A61K 31/505* (2006.01)

(52) U.S. Cl. ............ 514/259; 424/409; 424/420; 424/484; 424/485; 424/78.18; 523/122

(58) Field of Classification Search ........ 523/122; 525/7; 424/409, 420, 484, 485, 78.18; 514/259
See application file for complete search history.

(56) References Cited

U.S. PATENT DOCUMENTS

| | | | |
|---|---|---|---|
| 2,895,930 A | 7/1959 | Milton | |
| 3,806,479 A | 4/1974 | Yapp et al. | |
| 3,978,203 A | 8/1976 | Wise | |
| 3,997,512 A | 12/1976 | Casey et al. | |
| 4,048,256 A | 9/1977 | Casey et al. | |
| 4,076,798 A | 2/1978 | Casey et al. | |
| 4,095,600 A | 6/1978 | Casey et al. | |
| 4,118,470 A | 10/1978 | Casey et al. | |
| 4,122,129 A | 10/1978 | Casey et al. | |
| 4,384,975 A | 5/1983 | Fong | |
| 4,419,139 A | 12/1983 | Gooch et al. | |
| 4,568,559 A | 2/1986 | Nuwayser et al. | |
| 5,137,743 A | 8/1992 | Zaks et al. | |
| 5,155,246 A | 10/1992 | Naskar et al. | |
| 5,219,980 A | 6/1993 | Swidler | |
| 5,306,311 A | 4/1994 | Stone et al. | |
| 5,308,623 A | 5/1994 | Fues et al. | |
| 5,360,626 A | 11/1994 | Iyengar et al. | |
| 5,411,554 A | 5/1995 | Scopelianos et al. | |
| 5,442,033 A | 8/1995 | Bezwada et al. | |
| 5,464,929 A | 11/1995 | Bezwada et al. | |
| 5,599,852 A | 2/1997 | Scopelianos et al. | |
| 5,607,687 A | 3/1997 | Bezwada et al. | |
| 5,618,552 A | 4/1997 | Bezwada et al. | |
| 5,628,993 A | 5/1997 | Yamagata et al. | |
| 5,631,015 A | 5/1997 | Bezwada et al. | |
| 5,653,992 A | 8/1997 | Bezwada et al. | |
| 5,670,478 A | 9/1997 | Stuchlik et al. | |

(Continued)

FOREIGN PATENT DOCUMENTS

EP 0422209 B1 3/1995

(Continued)

OTHER PUBLICATIONS

European Search Report for EP 02 25 4564 dated Oct. 24, 2002.

(Continued)

*Primary Examiner*—Neil S. Levy (57) ABSTRACT

The present invention is directed to medical devices, pharmaceutical or agricultural compositions, and seeds, each containing a synthetic, bioabsorbable, biocompatible polymeric wax that is the reaction product of a polybasic acid or derivative thereof, a polyol and a fatty acid, the polymeric wax having a melting point less than about 70° C., as determined by differential scanning calorimetry.

12 Claims, 6 Drawing Sheets

U.S. PATENT DOCUMENTS

| | | | |
|---|---|---|---|
| 5,698,213 A | 12/1997 | Jamiolkowski et al. | |
| 5,700,583 A | 12/1997 | Jamiolkowski et al. | |
| 5,725,881 A | 3/1998 | Buchholz et al. | |
| 5,728,752 A | 3/1998 | Scopelianos et al. | |
| 5,750,100 A | 5/1998 | Yamagata et al. | |
| 5,753,234 A | 5/1998 | Lee et al. | |
| 5,824,333 A | 10/1998 | Scopelianos et al. | |
| 5,859,150 A | 1/1999 | Jamiolkowski et al. | |
| 5,998,552 A | 12/1999 | Gruber et al. | |
| 6,074,660 A | 6/2000 | Jamiolkowski et al. | |
| 6,100,346 A | 8/2000 | Jamiolkowski et al. | |
| 6,110,501 A * | 8/2000 | Redding, Jr. et al. | 424/490 |
| 6,114,458 A | 9/2000 | Hawker et al. | |
| 6,120,787 A | 9/2000 | Gustafsson et al. | |
| 6,121,398 A | 9/2000 | Wool et al. | |
| 6,147,168 A | 11/2000 | Jamiolkowski et al. | |
| 6,224,894 B1 | 5/2001 | Jamiolkowski et al. | |
| 6,251,435 B1 | 6/2001 | Jamiolkowski et al. | |
| 6,268,329 B1 | 7/2001 | Markussen | |
| 6,335,383 B1 | 1/2002 | Scopelianos et al. | |
| 2001/0007771 A1 | 7/2001 | Sullivan et al. | |
| 2001/0021377 A1 | 9/2001 | Jamiolkowski et al. | |
| 2003/0185752 A1 | 10/2003 | Nathan et al. | |

FOREIGN PATENT DOCUMENTS

| | | |
|---|---|---|
| EP | 841361 A1 | 5/1995 |
| EP | 747072 A | 12/1996 |
| EP | 1270024 A | 1/2003 |
| WO | WO 88/03785 A1 | 6/1988 |
| WO | WO 89/08694 A1 | 9/1989 |
| WO | WO 90/12604 A1 | 11/1990 |
| WO | WO 92/12645 A1 | 8/1992 |
| WO | WO 93/08850 A1 | 5/1993 |
| WO | WO 94/25079 A1 | 11/1994 |
| WO | WO 94/15079 A1 | 11/1995 |
| WO | WO 95/33821 A1 | 12/1995 |
| WO | WO 97/09367 A | 3/1997 |
| WO | WO 97/23606 A1 | 7/1997 |
| WO | WO 95/22318 A1 | 8/1997 |
| WO | WO 99/29303 A1 | 6/1999 |
| WO | WO 00/02950 A1 | 1/2000 |
| WO | WO 00/35511 A | 6/2000 |
| WO | WO 00/44808 A1 | 8/2000 |
| WO | WO 01/07486 A1 | 2/2001 |
| WO | WO 01/76649 A | 10/2001 |

OTHER PUBLICATIONS

Brian Parkyn F. Lamb and B. V. Clifton, "Polyesters vol. 2 Unsaturated Polyester Plasticisers," London Iliffe Books Ltd., New York American Elsevier ublishing Company, Inc., 1967 pp. 107-122.

Temple C. Patton, "Alkyd Resin Technology—Formulating Techniques and Allied Calculations," Interscience Publshers, a of John Wiley and Sons, New York—London 1962, pp. 13-31.

Database WPI Week 199430 Derwent Publications Ltd., London, GB; an 1994-248859 XP002256761 & WO 94 15591 A. (Hisamitsu), Jul. 12, 1994 abstract.

Emiko Koyama, Fumio Sanda, and Takeshi Endo, "Synthesis of Poly(ester-amide)s Derived from Optically Active Amino Alcohols," Macromol. Symp., 122, 275-280 (1997).

Emiko Koyama, Fumio Sanda, and Takeshi Endo, "Polycondensations of Hydroxycarboxylic Acids Derived from Optically Active Aminoalcohols and Acid Anhydrides—Synthesis of Functional Poly(ester-amide)s," Journal of Polymer Science: Part A: Polymer Chemistry 35, 345-352 (1997).

Donald L. Elbert, Alison B. Pratt, Matthias P. Lutolf, Sven Halstenberg, Jeffrey A. Hubbell, "Protein Delivery from Materials Formed by Self-selective Conjugate Addition Reactions," Journal of Controlled Relaase, 76, 11-25 (2001).

* cited by examiner

COMPOSITION AND MEDICAL DEVICES UTILIZING BIOABSORBABLE POLYMERIC WAXES

FIELD OF THE INVENTION

The present invention relates to bioabsorbable and biocompatible polymeric waxes for use in pharmaceutical, agricultural and medical applications.

BACKGROUND OF THE INVENTION

Both natural and synthetic polymers, including homopolymers and copolymers, which are both biocompatible and absorbable in vivo are known for use in the manufacture of medical devices that are implanted in body tissue and absorb over time. Examples of such medical devices include suture anchor devices, sutures, staples, surgical tacks, clips, plates and screws, drug delivery devices, adhesion prevention films and foams, and tissue adhesives.

Natural polymers may include catgut, cellulose derivatives and collagen. Natural polymers typically absorb by an enzymatic degradation process in the body.

Synthetic polymers may include aliphatic polyesters, polyanhydrides and poly(orthoester)s. Synthetic absorbable polymers typically degrade by a hydrolytic mechanism. Such synthetic absorbable polymers include homopolymers, such as poly(glycolide), poly(lactide), poly(ε-caprolactone), poly(trimethylene carbonate) and poly(p-dioxanone), and copolymers, such as poly(lactide-co-glycolide), poly(ε-caprolactone-co-glycolide), and poly(glycolide-co-trimethylene carbonate). The polymers may be statistically random copolymers, segmented copolymers, block copolymers or graft copolymers.

Alkyd-type polyesters prepared by the polycondensation of a polyol, polyacid and fatty acid are used in the coating industry in a variety of products, including chemical resins, enamels, varnishes and paints. These polyesters also are used in the food industry to make texturized oils and emulsions for use as fat substitutes.

There is a great need for polymers for use in drug delivery and medical devices, where the polymers have both low melting temperatures and low viscosities upon melting, thus permitting for solvent-free processing techniques in preparation of medical devices and compositions, can crystallize rapidly, and biodegrade within 6 months.

SUMMARY OF THE INVENTION

The present invention is directed to medical devices, pharmaceutical and agricultural compositions, and seeds, each comprising a synthetic, bioabsorbable, biocompatible polymeric wax comprising the reaction product of a polybasic acid or derivative thereof, a fatty acid and a polyol, the polymeric wax having a melting point less than about 70° C., as determined by differential scanning calorimetry.

DETAILED DESCRIPTION OF THE INVENTION

Alkyd polymers have been prepared by several known methods. For example, alkyd-type polymers were prepared by Van Bemmelen (J. Prakt. Chem., 69 (1856) 84) by condensing succinic anhydride with glycerol. In the "Fatty Acid" method (see Parkyn, et al. Polyesters (1967), Iliffe Books, London, Vol. 2 and Patton, In: Alkyd Resins Technology, Wiley-Interscience New York (1962)), a fatty acid, a polyol and an anhydride are mixed together and allowed to react. The "Fatty Acid-Monoglyceride" method includes a first step of esterifying the fatty acid with glycerol and, when the first reaction is complete, adding an acid anhydride. The reaction mixture then is heated and the polymerization reaction takes place. In the "Oil-Monoglyceride" method, an oil is reacted with glycerol to form a mixture of mono-, di-, and triglycerides. This mixture then is polymerized by reacting with an acid anhydride.

The synthetic, bioabsorbable, biocompatible polymeric waxes utilized in the present invention are the reaction product of a polybasic acid or derivative thereof, a fatty acid, and a polyol, and may be classified as alkyd polyester waxes. As used herein, a wax is a solid, low-melting substance that is plastic when warm and, due to its relatively low molecular weight, is fluid when melted. Preferably, the polymeric waxes of the present invention are prepared by the polycondensation of a polybasic acid or derivative thereof and a monoglyceride, wherein the monoglyceride comprises reactive hydroxy groups and fatty acid groups. The expected hydrolysis byproducts are glycerol, dicarboxylic acid(s), and fatty acid(s), all of which are biocompatible. Preferably, the polymeric waxes utilized in the present invention will have a number average molecular weight between about 1,000 g/mole and about 100,000 g/mole, as determined by gel permeation chromatography. The polymeric waxes comprise an aliphatic polyester backbone with pendant fatty acid ester groups that crystallize rapidly, depending on the fatty acid chain length, and exhibit relatively low melting points, e.g. less than about 100° C., preferably less than about 70° C. More preferably, the melting point of the polymeric wax will be between about 25° C. and about 70° C. Typically, the polymeric waxes used in the present invention will be a solid at room temperature.

Fatty acids used to prepare polymeric waxes utilized in the present invention may be saturated or unsaturated and may vary in length from $C_{14}$ to $C_{30}$. Examples of such fatty acids include, without limitation, stearic acid, palmitic acid, myrisitic acid, caproic acid, decanoic acid, lauric acid, linoleic acid and oleic acid.

Polyols that can be used to prepare the polymeric waxes include, without limitation, glycols, polyglycerols, polyglycerol esters, glycerol, sugars and sugar alcohols. Glycerol is a preferred polyhydric alcohol due to its abundance and cost.

Monoglycerides which may be used to prepare polymeric waxes utilized in the present invention include, without limitation, monostearoyl glycerol, monopalmitoyl glycerol, monomyrisitoyl glycerol, monocaproyl glycerol, monodecanoyl glycerol, monolauroyl glycerol, monolinoleoyl glycerol, monooleoyl glycerol, and combinations thereof. Preferred monoglycerides include monostearoyl glycerol, monopalmitoyl glycerol and monomyrisitoyl glycerol.

Polybasic acids that can be used include natural multifunctional carboxylic acids, such as succinic, glutaric, adipic, pimelic, suberic, and sebacic acids; hydroxy acids, such as diglycolic, malic, tartaric and citric acids; and unsaturated acids, such as fumaric and maleic acids. Polybasic acid derivatives include anhydrides, such as succinic anhydride, diglycolic anhydride, glutaric anhydride and maleic anhydride, mixed anhydrides, esters, activated esters and acid halides. The multifunctional carboxylic acids listed above are preferred.

In certain embodiments of the invention, the polymeric wax may be prepared from the polybasic acid or derivative thereof, the monoglyceride and, additionally, at least on additional polyol selected from the group consisting of ethylene glycol, 1,2-propylene glycol, 1,3-propanediol, bis-2-hydroxyethyl ether, 1,4-butanediol, 1,5-pentanediol, 1,6-hexanediol, 1,8-octanediol, 1,10-decanediol, 1,12-dodecanediol, other diols, linear poly(ethylene glycol), branched poly(ethylene glycol), linear poly(propylene glycol), branched poly(propylene glycol), linear poly(ethylene-co-propylene glycol)s and branched poly(ethylene-co-propylene glycol)s.

In preparing the polymeric waxes utilized in the present invention, the particular chemical and mechanical properties required of the polymeric wax for a particular use must be considered. For example, changing the chemical composition can vary the physical and mechanical properties, including absorption times. Copolymers can be prepared by using mixtures of diols, triol, polyols, diacids, triacids, and different monoalkanoyl glycerides to match a desired set of properties. Similarly, blends of two or more alkyd polyesters may be prepared to tailor properties for different applications.

Alkyd polyester waxes of the present invention can be made more hydrophobic by increasing the length of the fatty acid side chain or the length of the diacid in the backbone, or by incorporating a long chain diol. Alternatively, alkyd polyester waxes of the present invention can be made more hydrophilic or amphiphilic by employing hydroxy acids, such as malic, tartaric and citric acids, or some oxadiacids, in the composition, or by employing poly(ethylene glycol)s or copolymers of polyethylene glycol and polypropylene glycol, commonly known as Pluronics, in the formation of segmented block copolymers.

Copolymers containing other linkages in addition to an ester linkage also may be synthesized; for example, ester-amides, ester-carbonates, ester-anhydrides and ester urethanes, to name a few.

Multifunctional monomers may be used to produce cross-linked polymeric wax networks. Alternatively, double bonds may be introduced by using polyols, polyacids or fatty acids containing at least one double bond to allow photocrosslinking. Hydrogels may be prepared using this approach provided the polymer is sufficiently water soluble or swellable.

Functionalized polymeric waxes can be prepared by appropriate choice of monomers. Polymers having pendant hydroxyls can be synthesized using a hydroxy acid such as malic or tartaric acid in the synthesis. Polymers with pendent amines, carboxyls or other functional groups also may be synthesized. A variety of biologically active substances, hereinafter referred to as bioactive agents, can be covalently attached to these functional polymeric waxes by known coupling chemistry to give sustained release of the bioactive agent. As used herein, bioactive agent is meant to include those substances or materials that have a therapeutic effect on mammals, e.g. pharmaceutical compounds, or an adverse affect on, e.g. insects and fungi, such as pesticides, insecticides, fungicides, herbicides and germicides, as well as substances or materials used to enhance growth of plants, e.g. fertilizers.

One skilled in the art, once having the benefit of the disclosure herein, will be able to ascertain particular properties of the polymeric waxes required for particular purposes, and readily prepare polymeric waxes that provide such properties.

The polymerization of the alkyd polyester preferably is performed under melt polycondensation conditions in the presence of an organometallic catalyst at elevated temperatures. The organometallic catalyst preferably is a tin-based catalyst e.g. stannous octoate. The catalyst preferably will be present in the mixture at a molar ratio of polyol and polycarboxylic acid to catalyst in the range of from about 15,000/1 to 80,000/1. The reaction preferably is performed at a temperature no less than about 120° C. Higher polymerization temperatures may lead to further increases in the molecular weight of the copolymer, which may be desirable for numerous applications. The exact reaction conditions chosen will depend on numerous factors, including the properties of the polymer desired, the viscosity of the reaction mixture, and melting temperature of the polymer. The preferred reaction conditions of temperature, time and pressure can be readily determined by assessing these and other factors.

Generally, the reaction mixture will be maintained at about 180° C. The polymerization reaction can be allowed to proceed at this temperature until the desired molecular weight and percent conversion is achieved for the copolymer, which typically will take from about 15 minutes to 24 hours. Increasing the reaction temperature generally decreases the reaction time needed to achieve a particular molecular weight.

In another embodiment, copolymers of alkyd polyesters can be prepared by forming an alkyd polyester prepolymer polymerized under melt polycondensation conditions, then adding at least one lactone monomer or lactone prepolymer. The mixture then would be subjected to the desired conditions of temperature and time to copolymerize the prepolymer with the lactone monomers. The molecular weight of the prepolymer, as well as its composition, can be varied depending on the desired characteristic that the prepolymer is to impart to the copolymer. Those skilled in the art will recognize that the alkyd polyester prepolymers described herein can also be made from mixtures of more than one diol or dioxycarboxylic acid.

The polymers, copolymers and blends of the present invention can be cross-linked to affect mechanical properties. Cross-linking can be accomplished by the addition of cross-linking enhancers, irradiation, e.g. gamma-irradiation, or a combination of both. In particular, cross-linking can be used to control the amount of swelling that the materials of this invention experience in water.

One of the beneficial properties of the alkyd polyester of this invention is that the ester linkages are hydrolytically unstable, and therefore the polymer is bioabsorbable because it readily breaks down into small segments when exposed to moist body tissue. In this regard, while it is envisioned that co-reactants could be incorporated into the reaction mixture of the polybasic acid and the diol for the formation of the alkyd polyester, it is preferable that the reaction mixture does not contain a concentration of any co-reactant which would render the subsequently prepared polymer nonabsorbable. Preferably, the reaction mixture is substantially free of any such co-reactants if the resulting polymer is rendered nonabsorbable.

In one embodiment of the invention, the alkyd polyester waxes of the present invention can be used as a pharmaceutical carrier in a drug delivery matrix. To form the matrix, the polymeric wax would be mixed with an effective amount of a therapeutic agent to form the matrix. The variety of therapeutic agents that can be used in conjunction with the polymeric wax of the invention is vast. In general, therapeutic agents which may be administered via pharmaceutical compositions of the invention include, without limitation, antiinfectives, such as antibiotics and antiviral agents; analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators, including general coronary, peripheral and cerebral; central nervous system stimulants; cough and cold preparations, including decongestants; hormones, such as estradiol and other steroids, including corticosteroids; hypnotics; immunosuppressives; muscle relaxants; parasympatholytics; psychostimulants; sedatives; tranquilizers; naturally derived or genetically engineered proteins, polysaccharides, glycoproteins, or lipoproteins; oligonucleotides, antibodies, antigens, cholinergics, chemotherapeutics, hemostatics, clot dissolving agents, radioactive agents and cystostatics.

The drug delivery matrix may be administered in any suitable dosage form such as oral, parenteral, subcutaneously as an implant, vaginally or as a suppository. Matrix formulations containing the alkyd polyester may be formulated by mixing one or more therapeutic agents with the polymeric wax. The therapeutic agent may be present as a liquid, a finely divided solid, or any other appropriate physical form. Typically, but optionally, the matrix will include one or more additives, such as, but not limited to, nontoxic auxiliary substances such as diluents, carriers, excipients, stabilizers or the like. Other suitable additives may be formulated with the polymeric wax and pharmaceutically active agent or compound.

The amount of therapeutic agent will be dependent upon the particular drug employed and medical condition being treated. Typically, the amount of drug represents about 0.001% to about 70%, more typically about 0.001% to about 50%, most typically about 0.001% to about 20% by weight of the matrix.

The quantity and type of alkyd polyester wax incorporated into the parenteral will vary depending on the release profile desired and the amount of drug employed. The product may contain blends of polyesters to provide the desired release profile or consistency to a given formulation.

The alkyd polyester wax, upon contact with body fluids including blood or the like, undergoes gradual degradation, mainly through hydrolysis, with concomitant release of the dispersed drug for a sustained or extended period, as compared to the release from an isotonic saline solution. This can result in prolonged delivery, e.g. over about 1 to about 2,000 hours, preferably about 2 to about 800 hours) of effective amounts, e.g. 0.0001 mg/kg/hour to 10 mg/kg/hour) of the drug. This dosage form can be administered as is necessary depending on the subject being treated, the severity of the affliction, the judgment of the prescribing physician, and the like.

Individual formulations of drugs and alkyd polyester wax may be tested in appropriate in vitro and in vivo models to achieve the desired drug release profiles. For example, a drug could be formulated with an alkyd polyester wax and orally administered to an animal. The drug release profile could then be monitored by appropriate means, such as by taking blood samples at specific times and assaying the samples for drug concentration. Following this or similar procedures, those skilled in the art will be able to formulate a variety of formulations.

In addition to compositions comprising therapeutic agents as set forth above, compositions according to the present invention also may comprise bioactive agents that are toxic to certain life forms, e.g. pesticides, insecticides, fungicides, herbicides and germicides, as well as fertilzers. In one embodiment of the invention, seeds may be coated with compositions comprising the polymeric waxes, with or without such bioactive agents present in the composition.

In a further embodiment of the present invention the polymeric waxes and blends thereof can be used in tissue engineering applications, e.g. as supports for cells. Appropriate tissue scaffolding structures are known in the art, such as the prosthetic articular cartilage described in U.S. Pat. No. 5,306,311, the porous biodegradable scaffolding described in WO 94/25079, and the prevascularized implants described in WO 93/08850 (all hereby incorporated by reference herein). Methods of seeding and/or culturing cells in tissue scaffoldings are also known in the art such as those methods disclosed in EPO 422 209 B1, WO 88/03785, WO 90/12604 and WO 95/33821 (all hereby incorporated by reference herein).

The polymers of this invention can be melt processed by numerous methods to prepare a vast array of useful devices. These polymers can be injection or compression molded to make implantable medical and surgical devices, especially wound closure devices. The preferred wound closure devices are surgical clips, staples and sutures.

Alternatively, the alkyd polyester waxes can be extruded to prepare filaments. The filaments thus produced may be fabricated into sutures or ligatures, attached to surgical needles, packaged, and sterilized by known techniques. The polymers of the present invention may be spun as multifilament yarn and woven or knitted to form sponges or gauze, (or non-woven sheets may be prepared) or used in conjunction with other molded compressive structures as prosthetic devices within the body of a human or animal where it is desirable that the structure have high tensile strength and desirable levels of compliance and/or ductility. Useful embodiments include tubes, including branched tubes, for artery, vein or intestinal repair, nerve splicing, tendon splicing, sheets for typing up and supporting damaged surface abrasions, particularly major abrasions, or areas where the skin and underlying tissues are damaged or surgically removed.

Additionally, the polymers can be molded to form films which, when sterilized, are useful as adhesion prevention barriers. Another alternative processing technique for the polymers of this invention includes solvent casting, particularly for those applications where a drug delivery matrix is desired.

In more detail, the surgical and medical uses of the filaments, films, and molded articles of the present invention include, but are not limited to, knitted products, woven or non-woven, and molded products including, but not limited to burn dressings, hernia patches, meshes, medicated dressings, fascial substitutes, gauze, fabric, sheet, felt or sponge for liver hemostasis, gauze bandages, arterial graft or substitutes, bandages for skin surfaces, suture knot clip, orthopedic pins, clamps, screws, and plates, clips, e.g. for vena cava, staples, hooks, buttons, and snaps, bone substitutes, e.g. as mandible prosthesis, intrauterine devices, e.g. as spermicidal devices, draining or testing tubes or capillaries, surgical instruments, vascular implants or supports, e.g. stents or grafts, or combinations thereof, vertebral discs, extracorporeal tubing for kidney and heart-lung machines, artificial skin, and supports for cells in tissue engineering applications.

In another embodiment, the polymeric wax is used to coat a surface of a surgical article to enhance the lubricity of the coated surface. The polymer may be applied as a coating using conventional techniques. For example, the polymer may be solubilized in a dilute solution of a volatile organic solvent, such as acetone, methanol, ethyl acetate or toluene, and then the article can be immersed in the solution to coat its surface. Once the surface is coated, the surgical article can be removed from the solution where it can be dried at an elevated temperature until the solvent and any residual reactants are removed.

Although it is contemplated that numerous surgical articles, including but not limited to endoscopic instruments, can be coated with the polymeric waxes of this invention to improve the surface properties of the article, the preferred surgical articles are surgical sutures and needles. The most preferred surgical article is a suture, most preferably attached to a needle. Preferably, the suture is a synthetic absorbable suture. These sutures are derived, for example, from homopolymers and copolymers of lactone monomers such as glycolide, lactide, including L-lactide D-lactide, meso-lactide and rac-lactide, ε-caprolactone, p-dioxanone, 1,4-dioxanone, 1,4-dioxepan-2-one, 1,5-dioxepan-2-one and trimethylene carbonate. The preferred suture is a braided multifilament suture composed of polyglycolide or poly (glycolide-co-lactide).

The amount of coating polymer to be applied on the surface of a braided suture can be readily determined empirically, and will depend on the particular copolymer and suture chosen. Ideally, the amount of coating copolymer applied to the surface of the suture may range from about 0.5 to about 30 percent of the weight of the coated suture, more preferably from about 1.0 to about 20 weight percent, most preferably from 1 to about 5 weight percent. If the amount of coating on the suture were greater than about 30 weight percent, then it may increase the risk that the coating may flake off when the suture is passed through tissue.

Sutures coated with the polymers of this invention are desirable because they have a more slippery feel, thus making it easier for the surgeon to slide a knot down the suture to the site of surgical trauma. In addition, the suture is more pliable, and therefore is easier for the surgeon to manipulate during use. These advantages are exhibited in comparison to sutures which do not have their surfaces coated with the polymer of this invention.

In another embodiment of the present invention when the article is a surgical needle, the amount of coating applied to the surface of the article is an amount which creates a layer with a thickness ranging preferably between about 2 to about 20 microns on the needle, more preferably about 4 to about 8 microns. If the amount of coating on the needle were such that the thickness of the coating layer was greater than about 20 microns, or if the thickness was less than about 2 microns, then the desired performance of the needle as it is passed through tissue may not be achieved.

In yet another embodiment, the medical device comprises a bone replacement material comprising the polymeric wax and an inorganic filler. The organic filler may be selected from alpha-tricalcium phosphate, beta-tricalcium phosphate, calcium carbonate, barium carbonate, calcium sulfate, barium sulfate, hydroxyapatite, and mixtures thereof. In certain embodiments the inorganic filler comprises a polymorph of calcium phosphate. Preferably, the inorganic filler is hydroxyapatite. The bone replacement materials may further comprise a therapeutic agent in a therapeutically effective amount, such a growth factor, to facilitate growth of bone tissue. Furthermore, the bone replacement material may comprise a biologically derived substance selected from the group consisting of demineralized bone, platelet rich plasma, bone marrow aspirate and bone fragments. The relative amounts of polymeric wax and inorganic filler may be determined readily by one skilled in the art by routine experimentation after having the benefit of this disclosure.

The examples set forth below are for illustration purposes only, and are not intended to limit the scope of the claimed invention in any way. Numerous additional embodiments within the scope and spirit of the invention will become readily apparent to those skilled in the art.

In the examples below, the synthesized polymeric waxes were characterized via differential scanning calorimetry (DSC), gel permeation chromatography (GPC), and nuclear magnetic resonance (NMR) spectroscopy. DSC measurements were performed on a 2920 Modulated Differential Scanning Calorimeter from TA Instruments using aluminum sample pans and sample weights of 5–10 mg. Samples were heated from room temperature to 100° C. at 10° C./minute; quenched to −40° C. at 30° C./minute followed by heating to 100° C. at 10° C./minute. For GPC, a Waters System with Millennium 32 Software and a 410 Refractive Index Detector were used. Molecular weights were determined relative to polystyrene standards using THF as the solvent. Proton NMR was obtained in deuterated chloroform on a 400 MHz NMR spectrometer using Varian software.

EXAMPLE 1

Synthesis of Poly(monostearoyl glycerol-co-succinate)

8.0 gms (22.3 mmoles) of monostearoyl glycerol was added to a dry 50 mL, single neck, round bottom flask. A stir bar was added and a nitrogen inlet adapter was attached. The reaction flask was placed in a room temperature oil bath and a nitrogen gas blanket was started. The flask was heated to 140° C., and 4.46 gms (44.6 mmoles) of succinic anhydride was added. The temperature was raised to 200° C. and maintained for 3 hours. After 3 hours the flask was removed from the oil bath to cool to room temperature. Once the solution crystallized, it was deglassed and cleaned of any glass fragments. The polymer was an amber colored solid.

DSC measurements found a melt temperature of 46.84° C., and a specific heat of 63.57 J/gm. GPC measurement determined a number average molecular weight of 2,688, and a weight average molecular weight of 5,848. The $^1$H NMR showed the following peaks: δ0.86 triplet (3H), 1.26 multiplet (28H), 1.61 multiplet (2H), 2.30 multiplet (2H), 2.65 multiplet (4H), 4.16 multiplet (2H), 4.34 multiplet (2H), and 5.28 multiplet (2H).

EXAMPLE 2

Synthesis of Poly(monostearoyl glycerol-co-succinate)

The same procedure as Example 1 was used, except the reaction was maintained at 200° C. for 22.5 hours.

DSC measurements found a melt temperature of 48.41° C., and a specific heat of 73.98 J/gm. GPC measurement determined a number average molecular weight of 2,546, and a weight average molecular weight of 43,002. The $^1$H NMR showed the same peaks as shown in Example 1.

EXAMPLE 3

Synthesis of Poly(monostearoyl glycerol-co-succinate) with 5% PEG 9.50 gm (26.49 mmoles) of monostearoyl-rac-glycerol and 247.5 uL (1.39 mmoles) of polyethylene glycol (Mw=200) were added to a dry 50 mL, single neck, round bottom flask. A stir bar was added and a nitrogen inlet adapter was attached. The flask was placed in a room temperature oil bath and a nitrogen flow was started. The temperature was raised to 140° C. Once at 140° C., 2.79 gm (27.89 mmoles) of succinic anhydride was added and the temperature was raised to 200° C. The top of the reactor was wrapped with heat tape. The reaction was kept at 200° C. for 21 hours. The reaction was removed from the oil bath and allowed to cool. Once the polymer crystallized, it was deglassed and cleaned of all glass pieces. The polymer was a light brown solid.

DSC measurements found a glass transition temperature of –33.59° C., a melt temperature of 50.42° C., and a specific heat of 85.18 J/gm. GPC measurement determined a number average molecular weight of 2,397, and a weight average molecular weight of 36,197. The $^1$H NMR showed the following peaks: δ0.86 triplet (3H); 1.28 multiplet (28); 1.61 multiplet (2H); 2.32 multiplet (2H); 2.66 multiplet (4H); 4.14 multiplet (2H); 4.34 multiplet (2H); 5.27 multiplet (1H).

EXAMPLE 4

Synthesis of Poly(monostearoyl glycerol-co-succinate) w/5% PEG

The same procedure as Example 3 was followed, except the reaction was kept at 200° C. for 3 hours.

DSC measurements found a glass transition temperature of 7.52° C., a melt temperature of 50.86° C., and a specific heat of 70.55 J/gm. GPC measurement determined a number average molecular weight of 1,828, and a weight average molecular weight of 3,855. The $^1$H NMR showed the same peaks as shown in Example 4.

EXAMPLE 5

Synthesis of Poly(monostearoyl glycerol-co-adipate)

20.01 gm (56.0 mmoles) of monostearoyl glycerol, 8.19 g (56.0 mmole) adipic acid and 11 μL of stannous octoate were added to a dry 100 mL, single neck, round bottom flask. A stirbar was added and a nitrogen inlet adapter was attached. The reaction flask was placed into a room temperature oil bath and a nitrogen blanket was applied. The flask was heated to 170° C. and held at this temperature for 24 hours. The flask was removed from the oil bath and allowed to cool to room temperature. The polymer was a brown solid. It was isolated by breaking the glass and cleaning off any glass fragments with a brush.

GPC measurement determined a number average molecular weight of 2000, and a weight average molecular weight of 6000. The $^1$H NMR showed the following peaks: δ 0.86 triplet (3H), 1.26 multiplet (28H), 1.65 multiplet (6H), 2.35 multiplet (6H), 4.16 multiplet (2H), 4.34 multiplet (1H), 5.28 multiplet (2H).

EXAMPLE 6

Synthesis of Poly(monostearoyl glycerol-co-glutarate)

20.0 gm (56.0 mmoles) of monostearoyl glycerol, 7.40 gm (56 mmole) glutaric acid, and 11 μL of stannous octoate were added to a dry 100 mL, single neck, round bottom flask. A stir bar was added and a nitrogen inlet adapter was attached. The reaction flask was placed in a room temperature oil bath and a constant nitrogen gas blanket was applied. The reaction was heated to 170° C. and held at this temperature for 24 hours. The flask was removed from the oil bath and allowed to cool to room temperature. Once the solution crystallized, it was deglassed and cleaned of any glass fragments. The solid was dark brown.

DSC measurements found a melt temperature of 52.41° C., and a specific heat of 76.14 J/gm. GPC measurement determined a number average molecular weight of 2100, and a weight average molecular weight of 8800. The $^1$H NMR showed the following peaks: δ0.86 triplet (3H), 1.26 multiplet (28H), 1.61 multiplet (4H), 1.95 multiplet (2H), 2.32 multiplet (2H), 2.45 multiplet (4H), 4.16 multiplet (2H), 4.34 multiplet (1H), 5.28 multiplet (2H).

EXAMPLE 7

Sustained Release of Risperidone from Poly(monostearoyl glycerol-co-succinate) Microparticles in vitro Poly(monostearoyl glycerol-co-succinate) polymer was prepared as described in Example 2. 10 gms of the polymer was placed in a 50 mL beaker and heated to 110° C. to melt the polymer. 3.34 gms of a drug in the form of a powder, Risperidone, sold by Janssen Pharmaceutica Inc., Beerse, Belgium, under the tradename RISPERDAL, was dispersed and suspended into the polymer melt using a magnetic stirrer to form a 25% drug in polymer blend. A gradient heating mechanism was used to limit the exposure of the drug to the polymer melt at elevated temperature to few seconds.

The drug/polymer blend was converted to drug/polymer microparticles on a rotating disk apparatus. The drug/polymer blend first was equilibrated to 110° C. and then fed at a controlled rate of 3.5 gms/sec to the center of a 4-inch rotary disk that was run at 8000 RPM. The disk surface was heated using an induction heating mechanism to 130° C. to ensure that the drug/polymer blend was in a liquid state on the surface of the disk. The rotation of the disk caused a thin liquid film of drug/polymer blend to be formed on the surface the disk. The liquid film was thrown radially outward from the surface of the disk and droplets solidified upon contact with nitrogen in the rotating disk apparatus chamber to form drug/polymer microparticles. The processing was done under a nitrogen blanket to prevent polymer degradation at elevated temperatures. The solid microparticles were then collected using a cyclone separator. The microparticles made using this process had a mean particle size of about 100 μm.

In vitro release studies were performed with these microparticles in a buffer medium under physiological conditions. Approximately 20 mg of microparticles were placed in 50 mL test tubes. 30 ml of phosphate buffered saline solution was added to the test tubes. The test tubes were placed in a constant temperature water bath, and kept at 37° C. for the duration of the test. To determine drug release from the microparticles at each time point, 5 mL of buffer was removed and filtered through a 0.2 μm filter. The amount of drug released was determined by HPLC measurements on an HP1100 instrument against risperidone standards.

Figure 1:
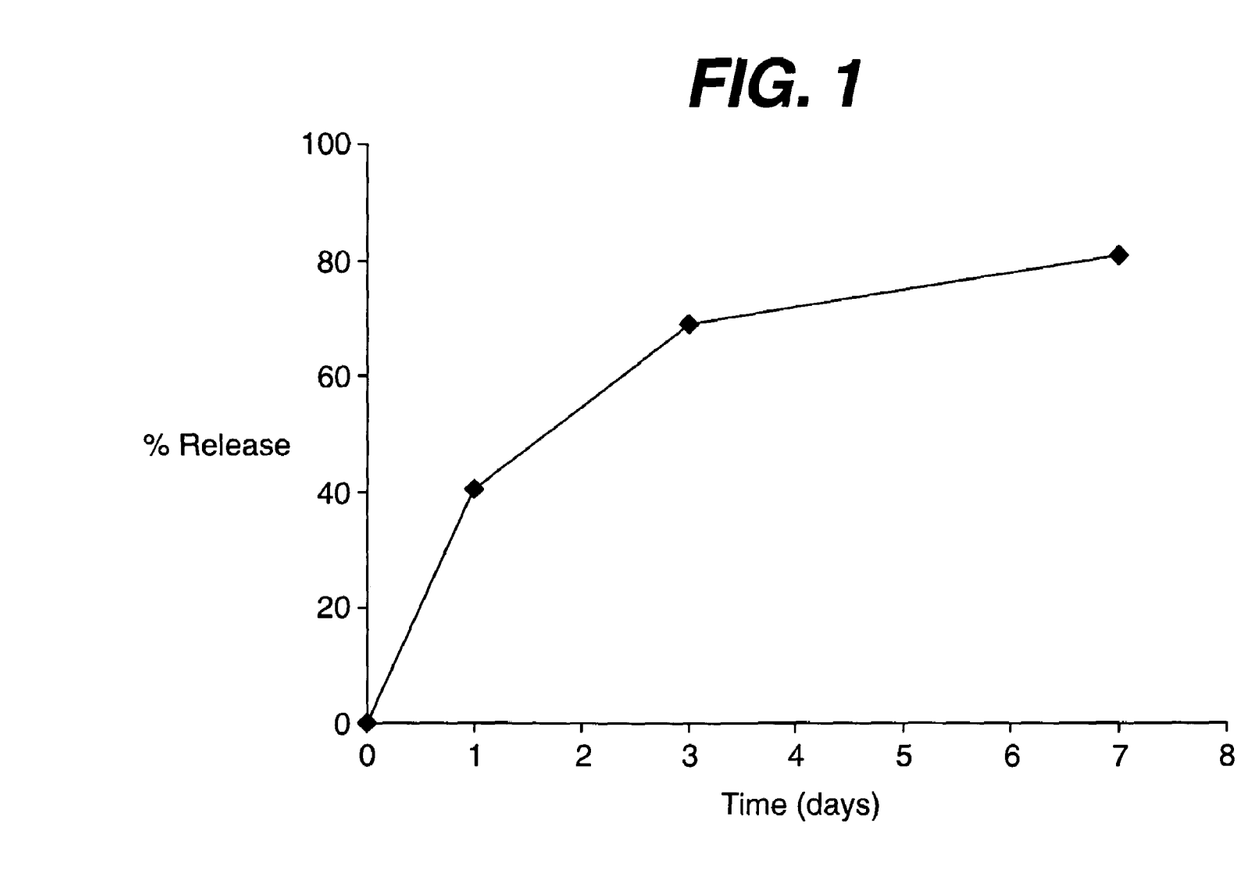
FIG. 1 is a plot of sustained release of Risperidone from poly(monostearoyl glycerol-co-succinate) microparticles in vitro.

In vitro release from the 25% drug in polymer microparticles is shown on FIG. 1. The figure shows 80% of the drug is released over a seven-day period.

EXAMPLE 8

Sustained Release of Risperidone Pamoate from Poly(monostearoyl glycerol-co-succinate) Microparticles in vitro Poly(monostearoyl glycerol-co-succinate) polymer was prepared as described in Example 2. Appropriate amounts of polymer were melted as described in Example 7, and blended with amounts of a drug, Risperidone Pamoate, as described in Example 8, to form 25% and 32% drug in polymer blends.

Figure 2:
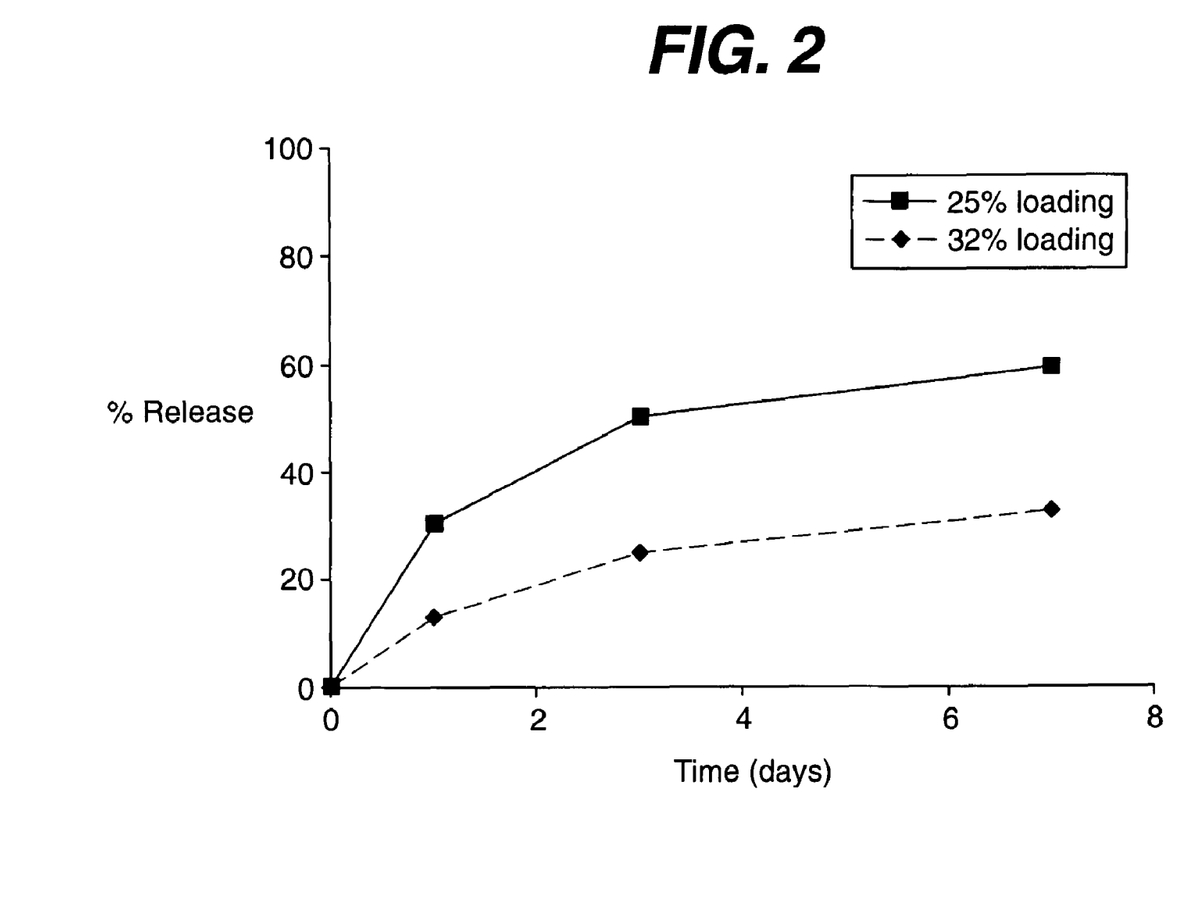
FIG. 2 is a plot of sustained release of Risperidone Pamoate from poly(monostearoyl glycerol-co-succinate) microparticles in vitro.

The drug/polymer blend was converted to drug/polymer microparticles on a rotating disk apparatus and in vitro release studies were performed with these microparticles in a buffer medium at physiological conditions as described in Example 7. Release from the 25% and 32% drug in polymer microparticles is shown on FIG. 2. The figure shows an approximate release of 60 and 25% of the drug over a seven-day period for 25% and 32% drug in polymer microparticles, respectively.

EXAMPLE 9

Sustained Release of Risperidone Pamoate from Poly(monostearoyl glycerol-co-succinate) Microparticles in vivo A single dose intramuscular pharmacokinetic study was performed in Beagle dogs using Risperidone Pamoate from poly(monostearoyl glycerol-co-succinate) microparticles. The animals utilized in this study were handled and maintained in accordance with current requirements of the Animal Welfare Act. Compliance with the above Public Laws was accomplished by adhering to the Animal Welfare regulations (9 CFR) and conforming to the current standards promulgated in the Guide for the Care and Use of Laboratory Animals.

25% and 32% drug in polymer microparticles were formed as described in Example 8. The microparticles were administered at a 5 mg/kg dose using an aqueous vehicle (hyaluronic acid) for injection. The mean plasma concentration values as a function of time were determined via HPLC.

Figure 3:
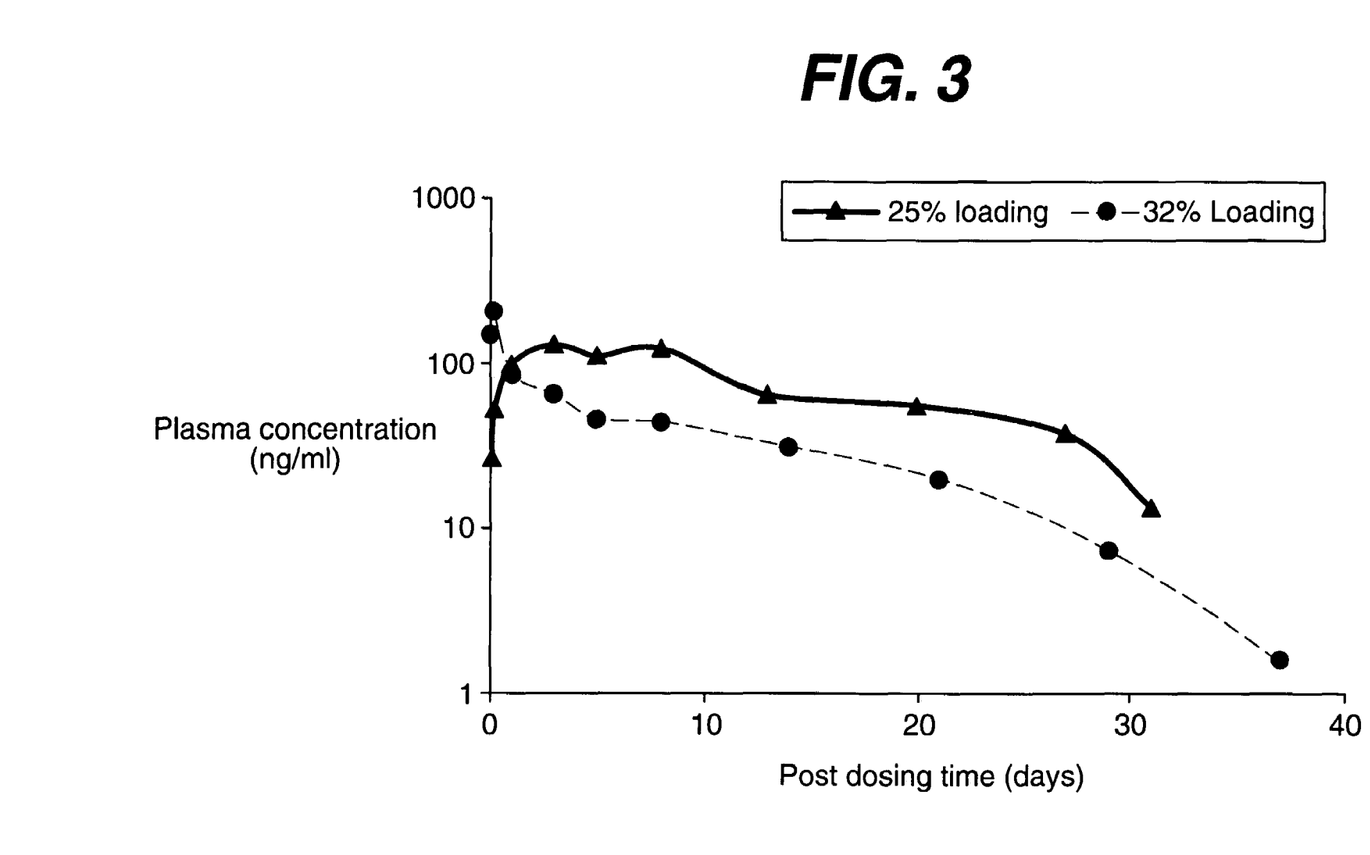
FIG. 3 is a plot of sustained release of Risperidone Pamoate from poly(monostearoyl glycerol-co-succinate) microparticles in vivo.

The mean plasma concentration values as a function of time are shown in FIG. 3. Therapeutic levels are reached at 10 ng/mL. The figure shows that the 25% drug in polymer microparticles did not give a drug burst and provided 30 days of sustained release at therapeutic levels. The 32% drug in polymer microparticles appeared to give a small burst followed by over 21 days of sustained release at therapeutic levels.

EXAMPLE 10

Sustained Release of Risperidone from Poly(monostearoyl glycerol-co-succinate) Films in vitro Poly(monostearoyl glycerol-co-succinate) polymer was prepared as described in Example 2. 10 gms of the polymer was placed in a 50 mL beaker, and heated to 110° C. to melt the polymer. 4.25 gms of Risperidone drug in the form of a powder was dispersed and suspended into the polymer melt using a magnetic stirrer to form a 30% drug in polymer blend.

Films were prepared by melt compression of the drug/polymer blend using a Carver laboratory press (Model #2696 Fred S. Carver Inc., Menomonee Falls, Wis.). A 4"×4"×0.03" sheet of poly(tetrafluoroethylene), or PTFE, was placed on the bottom platen of the press. Approximately 2-gms of polymer blend was placed on the PTFE sheet. 250 μm metal shims were placed around the blend to control the thickness of the polymer blend film. The polymer blend and shims were covered with another 4"×4"×0.03" sheet of PTFE. The platen temperature was raised to 80° C., which is above the melt temperature of the polymer. The compression pressure was in the range of 1000–2000 psi and the hold time was 5 minutes. After 5 minutes, the system was cooled by circulating water around the compression mold.

Figure 4:
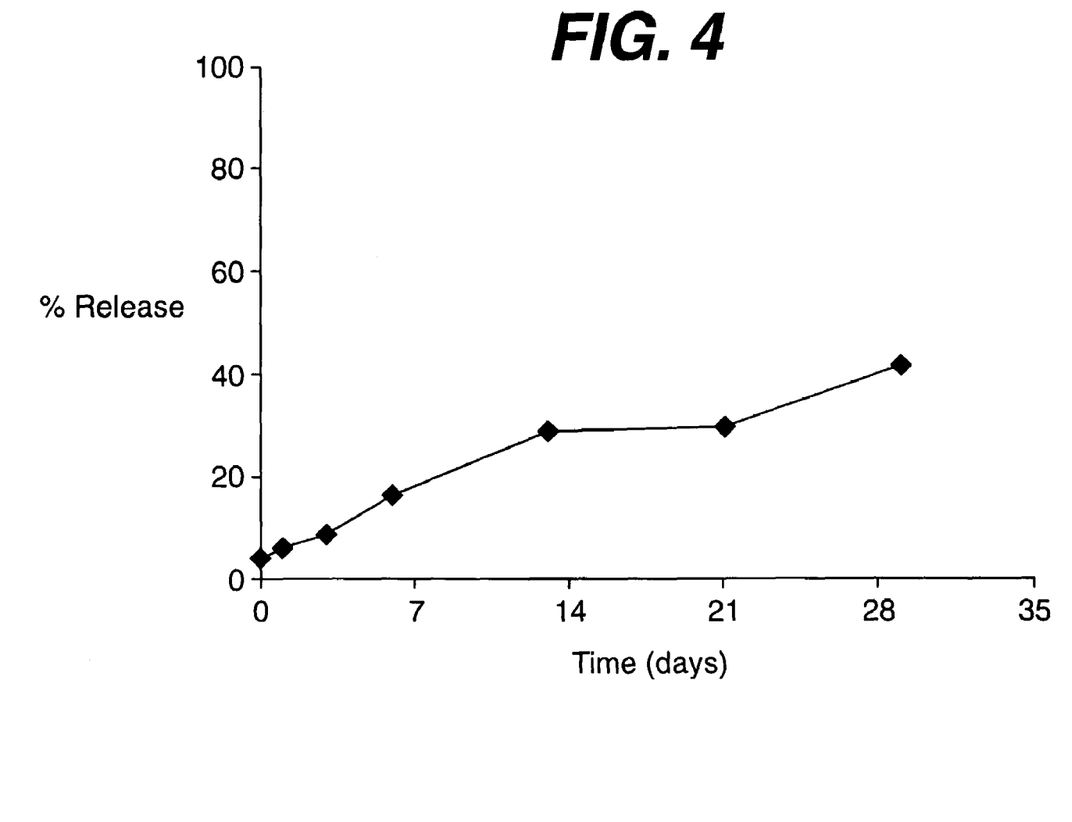
FIG. 4 is a plot of sustained release of Risperidone from poly(monostearoyl glycerol-co-succinate) films in vitro.

The compression molded polymer blend films were then cut into specimens of approximately 1-cm×1-cm×250 μm. Release studies were performed with 20 mg film specimens in a buffer medium at physiological conditions as described in Example 7. Release from 30% drug in polymer films is shown on FIG. 4. The figure shows an approximate release of 40% of the drug over a four-week period for 30% drug in polymer films.

EXAMPLE 11

Sustained Release of Risperidone from Poly(monostearoyl glycerol-co-succinate) Cylinders in vitro Poly(monostearoyl glycerol-co-succinate) polymer was prepared as described in Example 2. 8.0 gms of the polymer was placed in a 50 mL beaker, and heated to 110° C. to melt the polymer. 2 gms of Risperidone drug in the form of a powder was dispersed and suspended into the polymer melt using a magnetic stirrer under a nitrogen blanket to form a 20% drug in polymer blend.

The molten polymer/drug mixture was aspirated into capillary tubes with an inner diameter of 1 mm, and allowed to solidify at room temperature. The capillary tube was then quenched in liquid nitrogen for 1 to 2 minutes. Following quenching, the solidified cylinder was pushed out of the capillary tube using a metal rod. The cylinder was kept under vacuum for 48 hrs to remove any residual moisture and then cut into cylindrical specimens with dimensions of approximately 1 mm diameter by 1-cm length for drug release studies.

Figure 5:
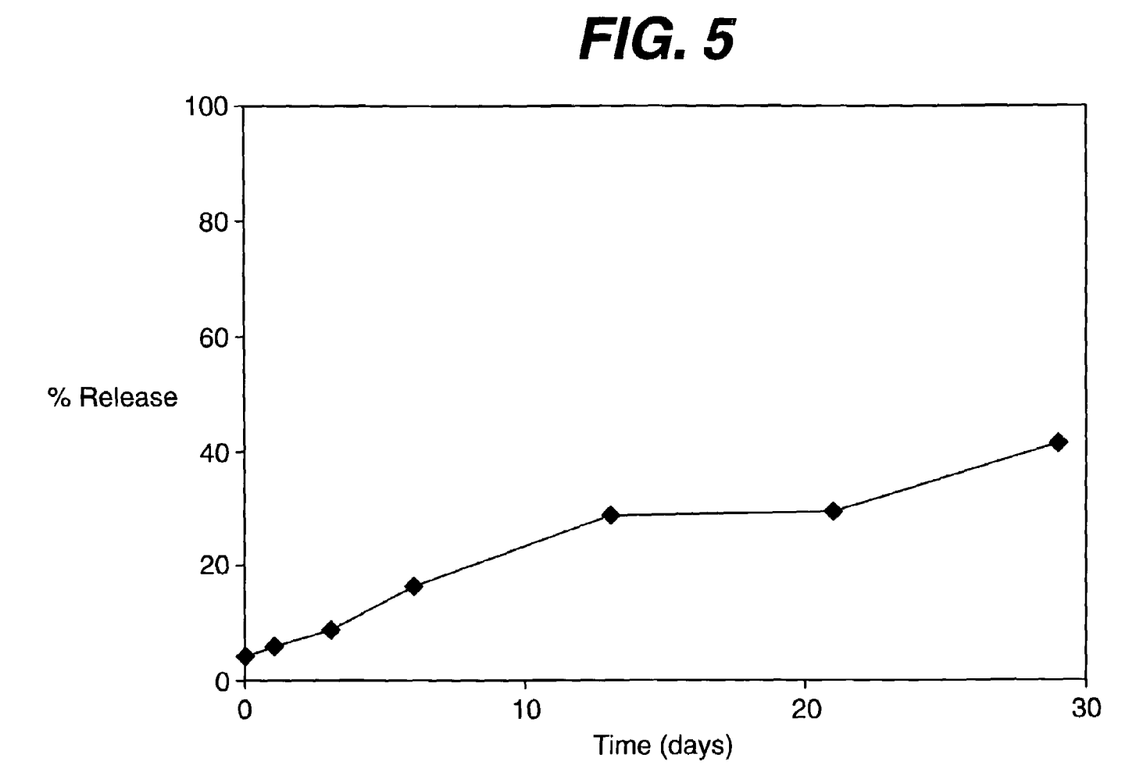
FIG. 5 is a plot of sustained release of Risperidone from poly(monostearoyl glycerol-co-succinate) cylinders in vitro.

Release studies were performed with these 20 mg cylindrical specimens in a buffer medium at physiological conditions as described in Example 7. Release from 20% drug in polymer cylinders is shown on FIG. 5. The figure shows an approximate release of 40% of the drug over a four-week period for 20% drug in polymer cylinders.

EXAMPLE 12

Sustained Release of Albumin from Poly(monostearoyl glycerol-co-succinate) in vitro Poly(monostearoyl glycerol-co-succinate) polymer was prepared as described in Example 1. 0.5 gms of the polymer was placed in a 5 mL vial and heated to 50° C. in an oil bath to melt the polymer. Separately, 0.05 gms of Bovine serum albumin (BSA), obtained from Sigma, St. Louis, Mo., was dissolved in 1 mL of deionized water to obtain a BSA solution. The melted microdispersion was removed from the oil bath, and 50 µL of the BSA solution was added to the melted microdispersion. The BSA solution/microdispersion melt mixture was stirred thoroughly by hand with a spatula until the mixture solidified. 3 mL of phosphate buffered saline (PBS) was added to the vial which was then transferred to a water bath maintained at 37° C.

At each time point, the PBS was removed completely and filtered through a 0.2 µm filter. The absorbance of the sample at 280 nm was measured on an HP8453 UV spectrophotometer against albumin standards.

Figure 6:
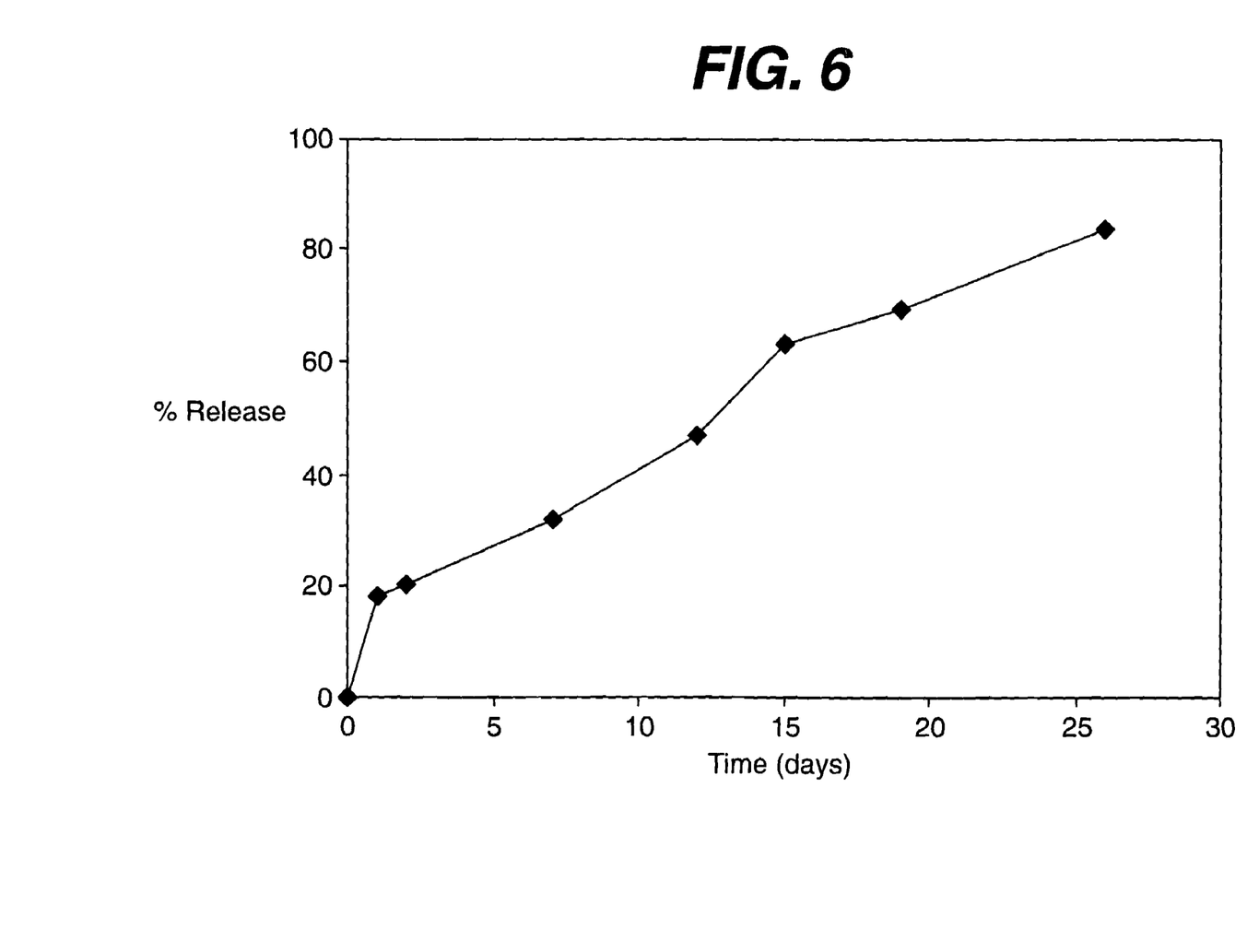
FIG. 6 is a plot of sustained release of Albumin from Poly(monostearoyl glycerol-co-succinate) in vitro.

Release from the BSA/polymer specimens is shown on FIG. 6. The figure shows release of approximately 80% of the BSA over a four-week period.

We claim:

1. A composition, comprising: a therapeutically effective amount of a therapeutic agent, and a polymeric wax comprising the reaction product of a polybasic acid or derivative thereof and a monoglyceride, said monoglyceride selected from the group consisting of monostearoyl glycerol, monopalmitoyl glycerol, monomyrisitoyl glycerol, monocaproyl glycerol, monodecanoyl, monolauroyl glycerol, monolinoleoyl glycerol and monooleoyl glycerol, said polymeric wax comprising an aliphatic polyester backbone having monoglyceride groups pending therefrom and having a melting point less than about 70° C., as determined by differential scanning calorimetry.

2. The composition of claim 1 wherein said polybasic acid or derivative thereof is selected from the group consisting of succinic acid, succinic anhydride, malic acid, tartaric acid, citric acid, diglycolic acid, diglycolic anhydride, glutaric acid, glutaric anhydride, adipic acid, pimelic acid, suberic acid, sebacic acid and derivatives thereof.

3. The composition of claim 2 wherein said polybasic acid derivative is succinic anhydride.

4. The composition of claim 2 wherein said polybasic acid is succinic acid.

5. The composition of claim 1 wherein said polymeric wax has a number average molecular weight between about 1,000 g/mole and about 100,000 g/mole, as measured by gel permeation chromatography using polystyrene standards.

6. The composition of claim 1 further comprising an aliphatic polyester prepared from the group of monomers consisting of glycolide, L-lactide, D-lactide, meso-lactide, rac-lactide, ε-caprolactone, trimethylene carbonate, p-dioxanone, 1,4-dioxanone, 1,4-dioxepan-2-one, 1,5-dioxepan-2-one and substituted derivatives thereof.

7. The composition of claim 1 wherein said polymeric wax has a melting point between about 25° C. and about 70° C.

8. A composition, comprising: a therapeutically effective amount of a therapeutic agent, and a polymeric wax copolymer comprising the reaction product of a fatty acid, a polyol, and at least two polybasic acids or derivatives thereof selected from the group consisting of succinic acid, succinic anhydride, malic acid, tartaric acid, citric acid, diglycolic acid and diglycolic anhydride, said polymeric wax copolymer comprising an aliphatic polyester backbone having fatty acid ester groups pending therefrom and having a melting point less than about 70° C., as determined by differential scanning calorimetry.

9. The composition of claim 8 wherein said polymeric wax copolymer comprises the reaction product of said polybasic acid or derivative thereof, and at least two monoglycerides selected from the group consisting of monostearoyl glycerol, monopalmitoyl glycerol, monomyrisitoyl glycerol, monocaproyl glycerol, monodecanoyl glycerol, monolauroyl glycerol, monolinoleoyl glycerol and monooleoyl glycerol.

10. The composition of claim 8 wherein said polymeric wax copolymer comprises the reaction product of said polybasic acid or derivative thereof, a monoglyceride selected from the group consisting of monostearoyl glycerol, monopalmitoyl glycerol, monomyrisitoyl glycerol, monocaproyl glycerol, monodecanoyl glycerol, monolauroyl glycerol, monolinoleoyl glycerol and monoolcoyl glycerol, and at least one additional polyol selected from the group consisting of ethylene glycol, 1,2-propylene glycol, 1,3-propanediol, bis-2-hydroxyethyl ether, 1,4-butanediol, 1,5-pentanediol, 1,6-hexanediol, 1,8-octanediol, 1,10-decanediol, 1,12-dodecanediol, linear poly(ethylene glycol), branched poly(ethylene glycol), linear poly(propylene glycol), branched poly(propylene glycol), linear poly(ethylene-co-propylene glycol)s and branched poly(ethylene-co-propylene glycol)s.

11. A composition, comprising: a therapeutically effective amount of risperidone, and a polymeric wax comprising the reaction product of a polybasic acid or derivative thereof, a fatty acid and a polyol, said polymeric wax comprising an aliphatic polyester backbone having fatty acid ester groups pending therefrom and having a melting point less than about 70° C., as determined by differential scanning calorimetry.

12. A composition, comprising: a therapeutically effective amount of a therapeutic agent, and a polymeric wax comprising the reaction product of a polybasic acid or derivative thereof, a fatty acid and a polyol, said polymeric wax comprising an aliphatic polyester backbone having fatty acid ester groups pending therefrom andilaving a melting point between about 25° C. and about 70° C., as determined by differential scanning calorimetry.

* * * * *